(12) United States Patent
Discko, Jr.

(10) Patent No.: US 7,243,789 B2
(45) Date of Patent: Jul. 17, 2007

(54) SINGLE PATIENT DOSE MEDICAMENT DISPENSER WITH APPLICATOR

(75) Inventor: John J. Discko, Jr., Trumbull, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 11/199,408

(22) Filed: Aug. 8, 2005

(65) Prior Publication Data

US 2005/0269219 A1    Dec. 8, 2005

Related U.S. Application Data

(60) Division of application No. 10/730,499, filed on Dec. 8, 2003, now Pat. No. 6,959,808, which is a division of application No. 09/976,225, filed on Oct. 12, 2001, now Pat. No. 6,685,013, which is a continuation-in-part of application No. 09/590,058, filed on Jun. 8, 2000, now Pat. No. 6,328,159, which is a continuation-in-part of application No. 09/342,756, filed on Jun. 29, 1999, now Pat. No. 6,116,414, which is a division of application No. 08/680,136, filed on Jul. 15, 1996, now Pat. No. 5,954,996, which is a continuation-in-part of application No. 08/275,003, filed on Jul. 13, 1994, now Pat. No. 5,660,273.

(51) Int. Cl.
*B65D 69/00* (2006.01)

(52) U.S. Cl. ........... 206/229; 206/15.3; 206/361; 206/209

(58) Field of Classification Search ........ 206/15.3, 206/209, 209.1, 229, 230, 361, 570, 564, 206/219, 222
See application file for complete search history.

(56) References Cited

U.S. PATENT DOCUMENTS

| | | | |
|---|---|---|---|
| 1,708,423 A | | 4/1929 | Maschane |
| 3,145,838 A | * | 8/1964 | Van Deusen ............ 206/221 |
| 3,415,361 A | * | 12/1968 | Chambliss et al. ........ 206/221 |
| 3,618,751 A | | 11/1971 | Rich |
| 3,759,375 A | | 9/1973 | Nappi |
| 3,835,834 A | | 9/1974 | Brown et al. |
| 3,873,735 A | | 3/1975 | Chalin et al. |
| 3,913,562 A | | 10/1975 | Moore et al. |
| 3,976,195 A | | 8/1976 | Cohen |
| 4,008,803 A | | 2/1977 | Smith |
| 4,200,193 A | | 4/1980 | Boyle |
| 4,458,812 A | * | 7/1984 | Dreier et al. ............ 206/221 |
| 4,739,881 A | | 4/1988 | Bruso |
| 4,746,614 A | | 5/1988 | Devaney, Jr. et al. |
| 4,786,534 A | | 11/1988 | Aiken |

(Continued)

FOREIGN PATENT DOCUMENTS

BE    890424    1/1982

(Continued)

*Primary Examiner*—David T. Fidei
(74) *Attorney, Agent, or Firm*—Fattibene and Fattibene; Paul A. Fattibene; Arthur T. Fattibene

(57) ABSTRACT

A unit dose package for applying a material with an applicator having a separate material and applicator portion. In one embodiment, a plurality of material wells is used to mix different materials to be dispensed with an applicator. In an embodiment the plurality of material wells are concentric. In another embodiment a portion of the cover is removable. In another embodiment, a material well is squeezed to dispense the material onto an applicator.

8 Claims, 16 Drawing Sheets

U.S. PATENT DOCUMENTS

| | | |
|---|---|---|
| 4,803,048 A | 2/1989 | Nason |
| 4,836,380 A | 6/1989 | Walter et al. |
| 4,838,851 A | 6/1989 | Shabo |
| 4,844,251 A | 7/1989 | Gueret |
| 4,858,821 A | 8/1989 | Bickelhaupt |
| 4,880,111 A | 11/1989 | Bagwell et al. |
| 4,889,228 A | 12/1989 | Gueret |
| 5,001,803 A | 3/1991 | Discko, Jr. |
| 5,106,297 A | 4/1992 | Discko, Jr. |
| 5,112,152 A | 5/1992 | McBride |
| 5,184,719 A | 2/1993 | Gordon |
| 5,240,415 A | 8/1993 | Haynie |
| 5,616,337 A | 4/1997 | Kasianovitz et al. |
| 5,660,273 A | 8/1997 | Discko, Jr. |
| 5,954,996 A | 9/1999 | Discko, Jr. |
| 6,105,761 A | 8/2000 | Peuker et al. |
| 6,116,414 A | 9/2000 | Discko, Jr. |
| 6,364,113 B1 | 4/2002 | Faasse et al. |
| 7,086,528 B2 * | 8/2006 | Raia et al. .................. 206/229 |

FOREIGN PATENT DOCUMENTS

| | | |
|---|---|---|
| DE | 31 22 237 | 1/1983 |
| DE | 33 10215 | 9/1984 |
| DE | 37 17512 | 12/1987 |
| DE | 10009629 | 9/2001 |
| DE | 100 56 212 | 5/2002 |
| EP | 0 049 553 | 7/1981 |
| EP | 0 095 630 B1 | 3/1988 |
| EP | 1153579 | 11/2001 |
| WO | WO 89 07053 | 8/1989 |
| WO | WO 0009416 | 2/2000 |

* cited by examiner

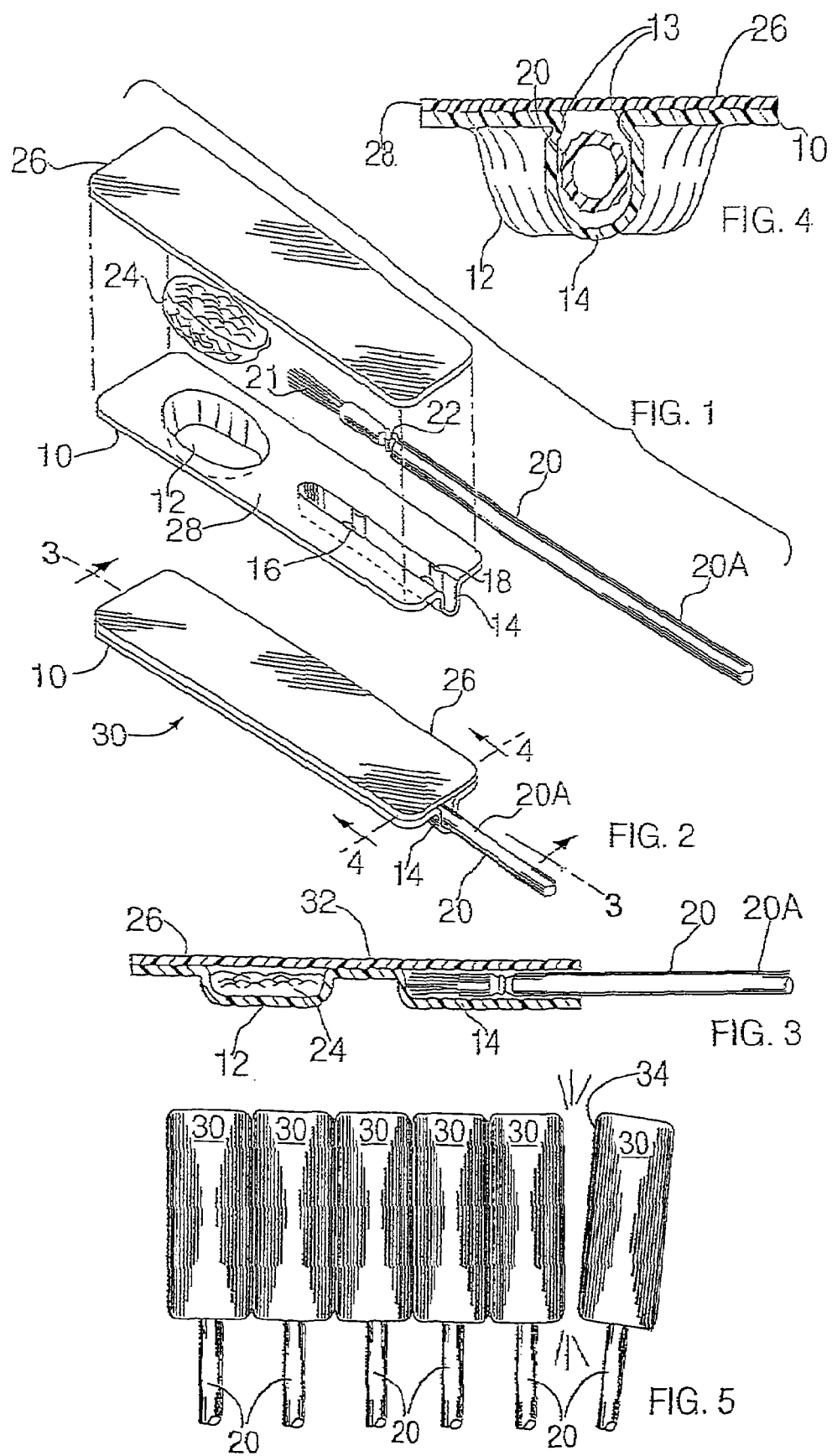

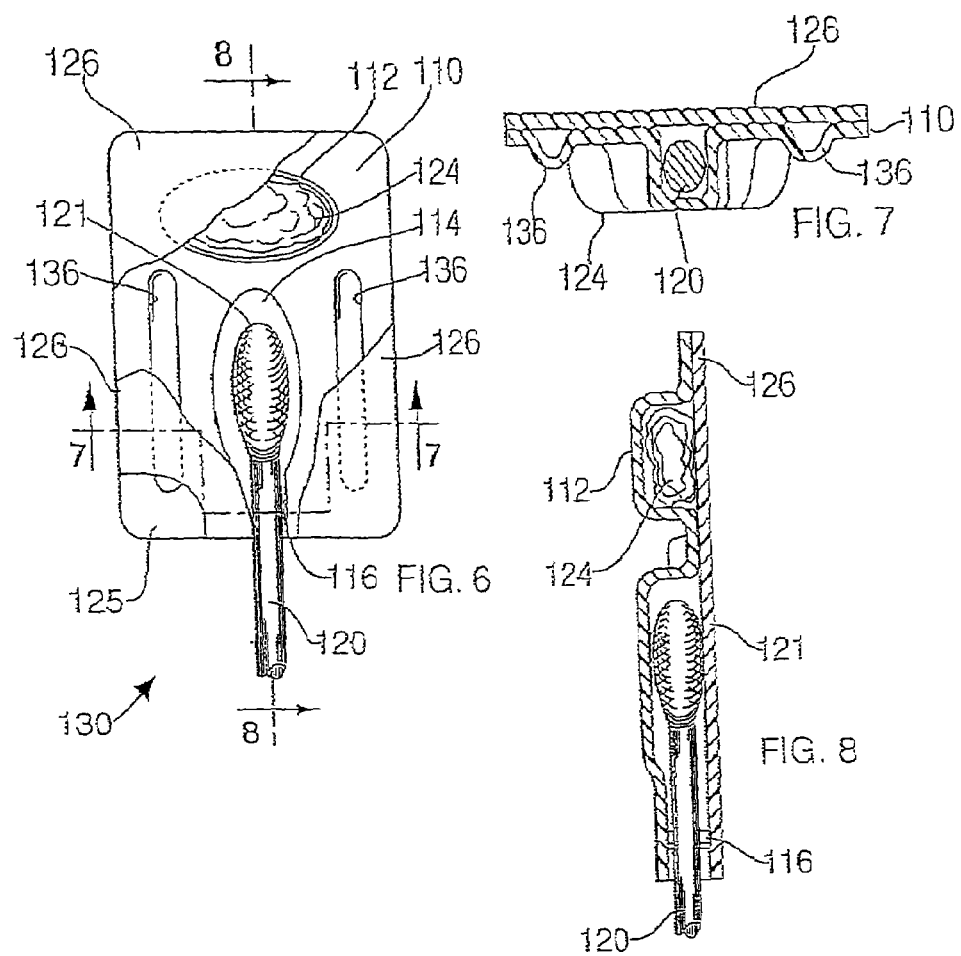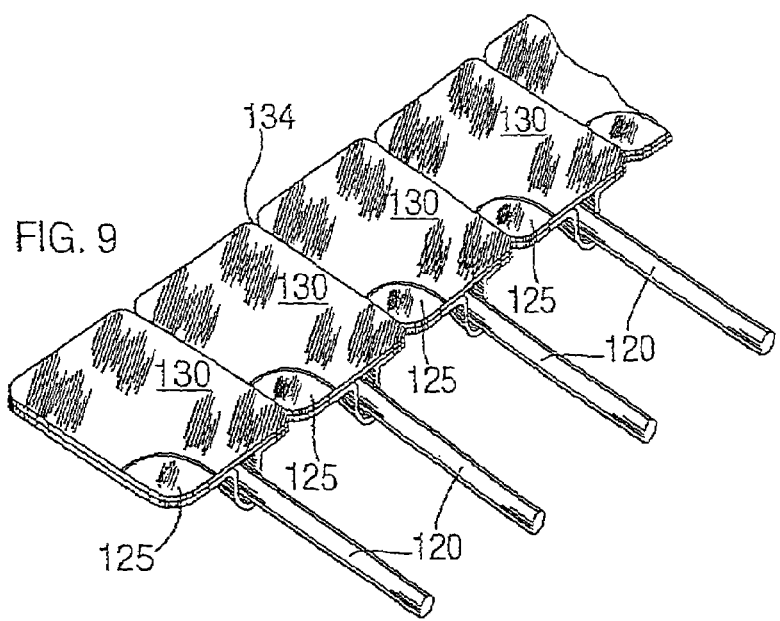

SINGLE PATIENT DOSE MEDICAMENT DISPENSER WITH APPLICATOR

RELATED APPLICATIONS

This application is a divisional application of application Ser. No. 10/730,499 filed Dec. 8, 2003 now U.S. Pat. No. 6,959,808, which is a divisional application of application Ser. No. 09/976,225 filed Oct. 12, 2001 entitled "Single Patient Dose Medicament Dispenser With Applicator", now U.S. Pat. No. 6,685,013, which is a continuation in part of application Ser. No. 09/590,058 filed Jun. 8, 2000 entitled "Single Patient Dose Medicament Dispenser With Applicator", now U.S. Pat. No. 6,328,159, which is a continuation in part of application Ser. No. 09/342,756 filed Jun. 29, 1999, entitled "Single Patient Dose Medicament Dispenser With Applicator", now U.S. Pat. No. 6,116,414, which is a divisional of application Ser. No. 08/680,136 filed Jul. 15, 1996 entitled "Dental Etch and Package Therefor", now U.S. Pat. No. 5,954,996, which is a continuation in part of application Ser. No. 08/275,003 filed Jul. 13, 1994 entitled "Single Patient Dose Medicament With Applicator", now U.S. Pat. No. 5,660,273, all of which are herein incorporated by reference.

FIELD OF THE INVENTION

The present invention relates generally to packaging for the dispensing of a medicament to be applied by an applicator, and more particularly to a disposable easy to use single patient dose medicament dispenser or package having an applicator.

BACKGROUND OF THE INVENTION

In many applications, and in particular the medical and dental professions, it is often necessary to apply a small amount of material with an applicator. Often, a dedicated applicator must be associated with the material to be applied. This is a result of the characteristics of the material to be applied or the desire and need to apply the material or a medicament to a single patient and then discarding the remainder to prevent the possibility of cross contamination between multiple patients. Presently in the medical profession, it is common to use a bulk container containing a medicament in combination with a multitude of disposable applicators such as brushes, spatulas, or cotton swabs. While in these applications the applicator is disposed of after each use, the possibility exists for the bulk container to become contaminated and therefore unusable, or if undetected, posing a health risk. Often it is difficult to determine whether or not a bulk container has become contaminated. Additionally, in many instances it is difficult to determine whether an applicator has been used and therefore contaminated. Often, applicators have been purchased and stored separately from the medicament or material to be applied. For example, a single use applicator is disclosed in U.S. Pat. No. 5,001,803 entitled "Disposable Dental Brush" issuing to Discko on Mar. 26, 1991, which is herein incorporated by reference. Therein disclosed is a disposable dental brush for applying various dental materials having an elongated handle with a tuft of bristles at one end. Additionally, various trays for holding and assisting in the dispensing of materials and medicaments are known. One such tray is disclosed in U.S. Pat. No. 5,106,297 entitled "Dental Bond Liquid and Sealant Tray" issuing to Discko on Apr. 21, 1992. Therein disclosed is a dental tray having depressions therein for holding a bottle of dental material and a plurality of distinctive shaped wells used for mixing. The common practice of dispensing a bulk material or medicament onto a tray that is supplied separately and in bulk and mixed with an applicator that is supplied separately and in bulk is often difficult and confusing. Often upon opening a bulk container, it requires some time to locate a tray as well as an applicator. Often one of the components necessary is missing or not readily available. Therefore, the procedure, once started, cannot be completed immediately. This is particularly disadvantageous in the application of materials or medicaments that require a specified amount of time in order to be effective. For example, this is true with materials or medicaments that are light sensitive or that have begun a chemical reaction that once started, cannot be stopped. One such system that has contributed to the ease of use in applying a medicament is disclosed in U.S. Pat. No. 5,240,415 entitled "Dental Bleach System Having Separately Compartmented Fumed Silica and Hydrogen Peroxide and Method of Using" issuing to Haynee on Aug. 31, 1993. Therein disclosed is a supply of fumed silica provided in a mixing chamber and a supply of hydrogen peroxide solution provided in an ampule packaged together with a spatula for mixing and applying the medicament after mixing to a dental surface. While the invention disclosed in this patent contributes to the easy use of medicaments, it constitutes a relatively large packaging system that is often difficult to open and use. Therefore, there is a need for a different packaging concept that will be easier to open and use, less costly to manufacture with less wasted material and provide easy handling.

SUMMARY OF THE INVENTION

The present invention is a single patient dose package for storing, dispensing, and applying a material or medicament that requires an applicator such as a brush, swab, spatula or the like. A tray is formed having a medicament well and an applicator well. The applicator well is configured to prevent contact with the medicament in the medicament well prior to the intended use and application of the medicament to the applicator in a particular procedure. The applicator well is formed to retain therein an applicator until ready for use. The applicator well is shorter than the applicator permitting a portion, i.e. the handle of the applicator to extend beyond the applicator well and one edge of the tray. A cover covers the tray, medicament well, and applicator well preventing contamination of the applicator and the medicament contained within the tray.

In one form of the invention, the medicament well is rendered squeezable whereby the medicament in the medicament well may be squeezed to extrude the medicament in the medicament well into an adjacent applicator well and onto the applicating end of the applicator therein without removing the cover. In another form of the invention, the applicator is provided with a piercing end by which the user may pierce or perforate the cover overlying the medicament well with the piercing end of the applicator and through which the applicating end of the applicator may be inserted to pick up the medicament to be applied. This technique is particularly suitable when the medicament in the medicament well is a liquid or fluent.

In the various embodiments disclosed, the applicating end of the applicator is releaseably retained within the application well in a manner to prohibit any unintentional separation of the applicator from the applicator well and whereby separation of the application may be intentionally achieved by applying a reasonable pulling force on the extended handle portion of the applicator.

Accordingly, it is an object of the present invention to provide a convenient, single patient dose package that is easy to use and/or open.

It is a further object of the present invention to prevent potential contamination of a medicament and the applicator due to prolonged exposure during storage prior to use.

It is an advantage of the present invention that the single dose package is easy to open.

It is a further advantage of the present invention that the single dose package with applicator requires a minimum amount of packaging material in the making thereof.

It is a feature of the present invention that a portion of the applicator extends beyond the tray and affixed cover.

It is a further feature of the present invention that a disposable applicator is conveniently associated with a single patient dose of medicament in a convenient, easy to use package.

It is another object of this invention to provide a medicament package with an applicator having an applicating end portion and a piercing end portion whereby the latter is used for piercing the cover overlying the medicament well.

Another object is to provide a medicament package having an applicator releaseably retained therein in a manner to prohibit any unintentional separation thereof.

These and other objects, advantages, and features will become readily apparent in view of the following more detailed description.

BRIEF DESCRIPTION OF THE DRAWINGS

FIG. 1 is an exploded perspective view of one embodiment of the invention.

FIG. 2 is an assembled perspective view of the embodiment illustrated in FIG. 1.

FIG. 3 is a cross section taken along line 3—3 in FIG. 2.

FIG. 4 is a cross section taken along line 4—4 in FIG. 2.

FIG. 5 illustrates a top view of a plurality of connected single packages of the embodiment of FIG. 1.

FIG. 6 is a plan view, partially sectioned, illustrating another embodiment of the invention.

FIG. 7 is a cross section taken along line 7—7 in FIG. 6.

FIG. 8 is a cross section taken along line 8—8 in FIG. 6.

FIG. 9 is a perspective top view illustrating a plurality of connected single packages of the embodiment of FIG. 6.

DETAILED DESCRIPTION OF THE PREFERRED EMBODIMENTS

Figure 10:
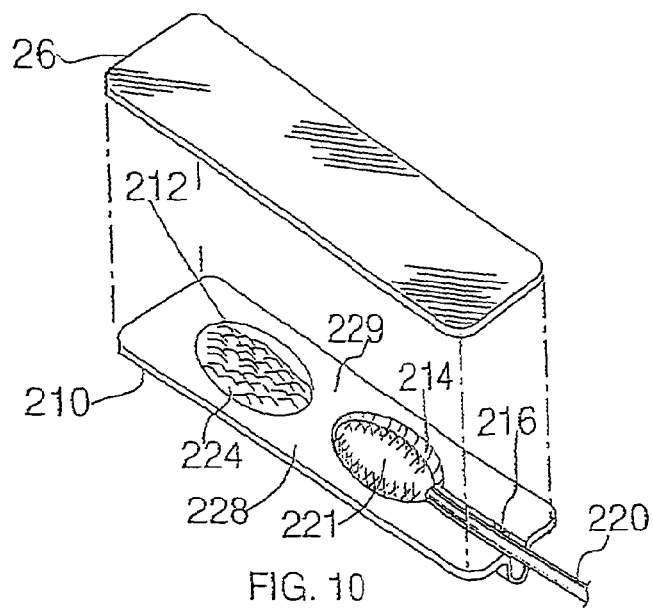
FIG. 10 is an exploded view of another embodiment of the invention.

FIG. 1 illustrates one embodiment of the present invention. A tray 10 has formed therein a material or medicament well 12 and an applicator well 14. Tray 10 may be made from a plastic material that is easily vacuum formed in order to make the medicament well 12 and applicator well 14 therein. Formed within applicator well 14 is a retainer 16 and a seal 18. The retainer 16 and seal 18 are protrusions that extend into the interior of the applicator well 14 a predetermined distance. The applicator well 14 is adapted to receive the applicating portion 21 of an applicator 20. Applicator as herein defined comprises a brush, spatula, cotton swab, sponge swab, a flock type swab and the like. Applicator 20 is illustrated as having a crimp 22 therein, and bristles 21. The applicator 20 may be a brush having construction similar to that disclosed in U.S. Pat. No. 5,001,803 entitled "Disposable Dental Brush" issuing to Discko on Mar. 26, 1991, which is herein incorporated by reference. The brush portion 21 of the applicator brush 20 fits within well 14 with the major portion of the brush applicator handle 20A extending beyond the tray 10. The retainer 16 is positioned to contact the crimp 22 on applicator brush 20. This helps to prevent the applicator brush 20 from being unintentionally removed from the applicator well 14. As shown, a substantial portion of the applicator or brush 20, i.e. the handle portion 20A, extends beyond the open end or edge of the applicator well 14. However, in some applications only a portion of applicator brush 20 sufficient to grasp easily need extent beyond the open end of the applicator well 14. Seal 18 at the end of applicator well 14 helps to prevent contamination from entering the open end of applicator well 14. A medicament 24 is placed within medicament well 12. The volume of medicament 24 placed within medicament well 12 is a volume that is sufficient to perform a specific procedure for a single patient, and may take into consideration the working time of the material or medicament 24. After insertion of the medicament 24 and the applicator or brush 20 within their respective wells, a cover 26 is affixed to top planar surface 28 of tray 10. The cover is a thin flexible sheet material, preferably made of either clear transparent or light opaque plastic material. This may be done with an adhesive or heat sealing. The adhesively affixing or heat sealing of the cover 26 seals the medicament 24, the applicator portion of the brush or applicator within the tray and also helps to hold the applicator or brush 20 within the applicator well 14.

FIG. 2 illustrates the present invention in assembled form. After assembly, a single patient dose or unit dose package 30 is formed. Cover 26 extends over the entire top surface of tray 10. The handle portion 20A of applicator brush 20 extends beyond the open end or edge of applicator well 14, yet is securely held therein. The extension of applicator handle 20A beyond the tray substantially reduces the amount of material normally required in a disposable single patient dose or unit dose type package requiring an applicating device. The applicator or brush 20 also acts as a handle for grasping the entire package. The extension of the applicator or brush 20 beyond the applicator well 14 also helps in removing the cover 26 which is often securely attached to the top surface of tray 10. The applicator handle 20A may be used to pry upward the cover 26. This is a particular advantage in that often during many medical procedures, rubber gloves are required which would otherwise make it extremely difficult to separate the cover 26 from the top surface of tray 10. Also, the applicator may be pulled axially out of the applicator well through the opened end 14, leaving the cover intact.

FIG. 3 illustrates, in this embodiment, that a continuous seal 32 is formed between the medicament well 12 and the applicator well 14. This assures that the medicament is positively contained in medicament well 12 and does not unintentionally contact applicator or brush 20 until the cover 26 is removed. Alternatively, the cover 26 need not be sealed to the tray in the area between the material well 12 and the applicator well and may be attached as described with respect to FIG. 11 so that the embodiment of FIG. 3 can then be made to function as described with respect to FIG. 12.

FIG. 4 more clearly illustrates the applicator well 14 formed within tray 10. The applicator well 14 has lips 13 that extend inward along the upper longitudinal edges of well 14 between protrusions 16 and 18 to firmly secure the applicator or brush 20 within the applicator well 14. The sides of the applicator well 14 are flexible, therefore permitting the applicator or brush 20 to be pushed through the opening past the lips 13. The distance between lips 13 is less than the diameter of the applicator or brush 20. While FIG. 4 illustrates a gap between cover 26 and the top surface of applicator or brush 20, often the cover 26 material is thin and flexible, and depending upon the sealing process used, the cover 26 may be forced downward contacting the top surface of the applicator or brush 20 further helping to retain the applicator or brush 20 within the applicator well 14 and sealing it from possible contamination. This is often the case when heat sealing is used in combination with a slight vacuum. In such event, the lips 13 may not be necessary.

FIG. 5 illustrates the present invention in the form of a plurality of single patient dose or unit dose packages 30 formed as a continuous strip or a plurality of connected packages 30 being frangibly connected together by a readily frangible connection 34. The individual single patient dose or unit dose package 30 may be easily snapped off at the frangible connection 34 for use. The feature of the present invention illustrated in FIG. 5 of providing a plurality of frangibly connected single patient dose or unit dose packages 30 is particularly applicable when a particular procedure may require a sequence of applications of the same or different material, in which case the number of applications or different materials for a given procedure is conveniently provided together. Additionally, the portion of the applicator or brush 20 that extends from the tray 10 may be used to correctly identify the sequence of application or material by color of the applicator or brush 20. A different color or shade being used for each different material or application.

FIGS. 6–9 illustrate another embodiment of the present invention. FIG. 6 illustrates a tray 110 having a medicament well 112 and an applicator well 114 formed therein. Within applicator well 114 is a retainer 116. Retainer 116 helps to hold an applicator swab 120. The applicator swab 120 has a cotton swab 121 on one end thereof. In this embodiment the cotton swab 121 contributes to holding the applicator swab 120 within the applicator well 114. The other end of applicator swab 120 extends beyond the open end or edge of applicator well 114. Also formed within the tray 110 are support ribs 136. The support ribs 136 add some rigidity to the tray 110 and permit the use of thinner stock material in forming the tray 110. The ribs 136 reduce the top surface area that is affixed to the cover 126. This helps removal of the cover 125. Medicament 124 is placed in the medicament well 112. A cover 126 covers the entire top surface of tray 110 except for the ribs 136. The cover 126 is typically a thin flexible sheet material as hereinbefore described that may be affixed with adhesive or thermally sealed to the top surface of tray 110. For illustration purposes only, the cover 126 illustrated in FIG. 6 has been sectioned. Typically, the cover 126 covers the entire top planar surface of tray 110, with the exception of exposed portion 125 and depressed ribs 136. The exposed portion 125 facilitates the removal of the cover 126. The tray 110 can be grasped by the exposed portion 125 while the applicator swab 120 is pried upward, facilitating removal of the cover 126. FIGS. 7–8 are cross section views more clearly illustrating the construction of this embodiment. FIG. 9 illustrates a plurality of single patient dose or unit dose packages 130 being connected with a frangible connection 134 as hereinbefore described.

Figure 11:
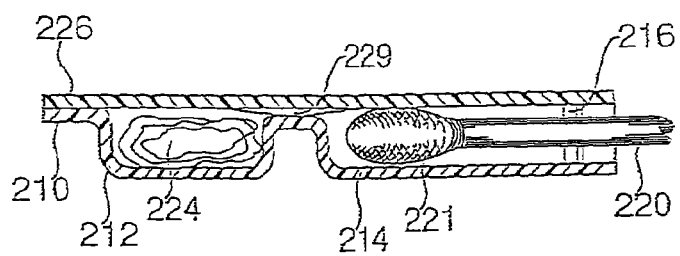
FIG. 11 is a cross section illustrating the embodiment illustrated in FIG. 10.
Figure 12:
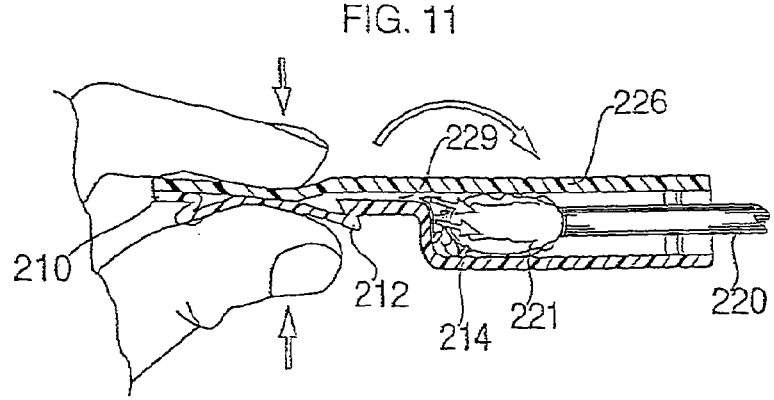
FIG. 12 is a cross section illustrating the embodiment of FIG. 10 in use.

FIGS. 10–12 illustrate another embodiment of the present invention. In this embodiment, tray 210 has a medicament well 212 and an applicator well 214 formed therein. Within applicator well 214 is formed a retainer 216. Retainer 216 also helps to seal the applicator well 214 from external contamination. An applicator swab 220 having a cotton swab 221 on one end thereof is placed within the applicator well 214. A portion of the applicator swab 220 extends beyond the open end or edge of applicator well 214. Placed within medicament well 212 is a medicament 224. Along the top surface of tray 210 is placed an adhesive 228. The adhesive is absent from a portion of the top surface of tray 210 at adhesive free section 229 extending between the respective wells 212 and 214. This adhesive free section forms a channel between the medicament well 212 and the applicator well 214. FIGS. 11 and 12 illustrate a section of the adhesive free section 229. Because there is no adhesive over a small width between the medicament well 212 and the applicator well 214, the medicament well 212 may be squeezed as illustrated in FIG. 12, with the cover 226 in place, forcing the medicament 224 to pass through the adhesive free section 229 and into the applicator well 214 and onto the cotton swab 221 of applicator swab 220. The applicator swab 220 is then removed for applying the medicament. It is understood that the applicator 220 by definition herein may include a bristle type brush, flocked type brush, spatula, sponge, and the like.

Figure 13:
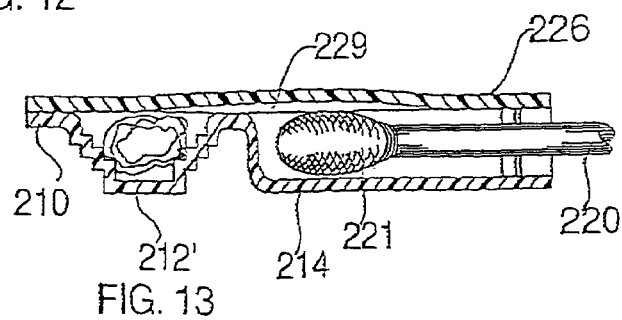
FIG. 13 is a cross section illustrating another embodiment of the invention of the type shown in FIG. 10.

FIG. 13 illustrates a slightly modified embodiment wherein the medicament well 212' has a slightly different structure to that illustrated in FIGS. 10–12. In FIG. 13 the medicament well 212' has a diminishing stepped or bellows structure that facilitates collapsing of the medicament well 212' when squeezed. The step structure is made of a plurality of substantially concentric wells with each adjacent well having a slightly smaller periphery or circumference.

Figure 14:
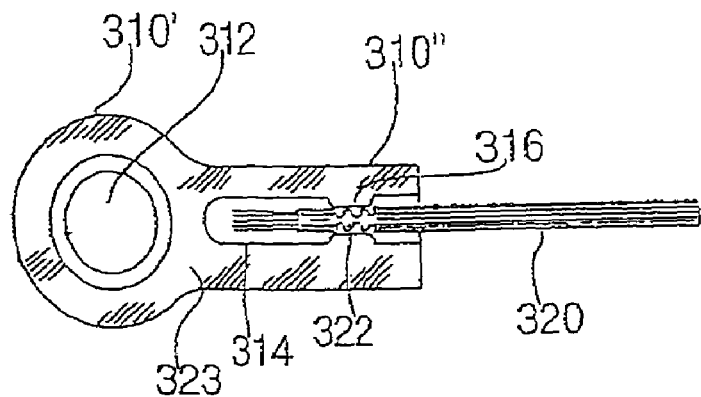
FIG. 14 is a plan view illustrating another embodiment of the invention.
Figure 15:
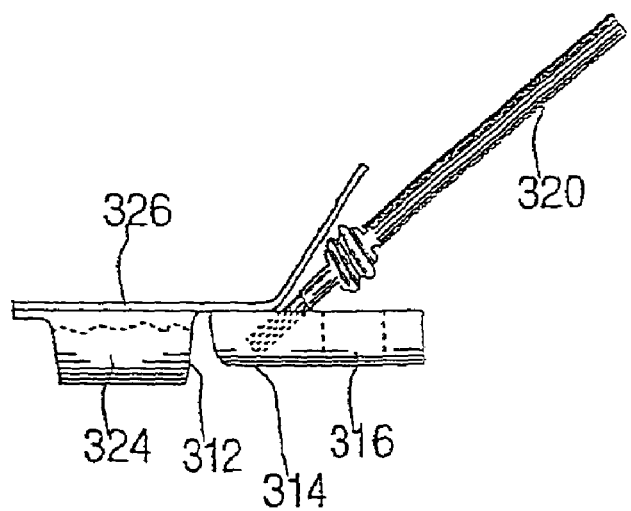
FIG. 15 is a front elevational view illustrating the operation of the embodiment illustrated in FIG. 14.

FIGS. 14–15 illustrate another embodiment of the present invention that further reduces to a minimum packaging material used in a single patient dose or a unit dose package. FIG. 14 illustrates a round head portion 310' having a rectangular tail portion 310". The round head portion 310' has a round medicament well 312 therein. The rectangular tail portion 310" has an elongated applicator well 314 formed therein. The applicator well 314 has a retainer portion 316 that extends inwardly within the applicator well 314. The retainer portion 316 also helps to seal the applicator well 314 from external contamination. The retainer portion 316 corresponds to a crimp 322 formed on the applicator or brush 320. A substantial portion, greater than one-half of the length, of the applicator or brush 320 extends beyond the open end or edge of the applicator well 314. Therefore, only a minimum amount of material is required in the package. The top surface 323 of the round head portion 310' and the rectangular tail portion 310" forms a sealing surface. It will be understood that the cover need not be sealed in the area between wells 312 and 314 as described with respect to FIGS. 10 to 13.

Figure 14A:
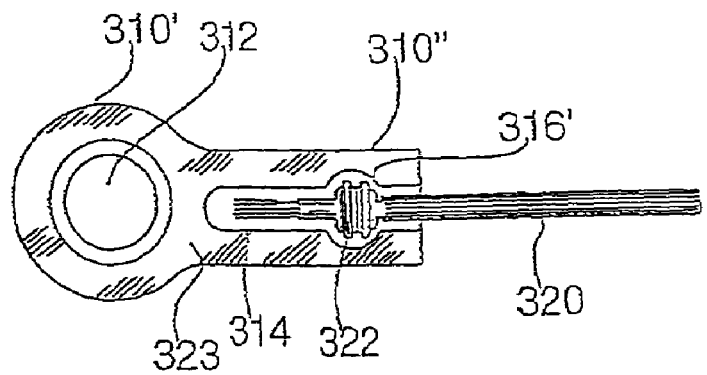
FIG. 14A is a plan view illustrating another embodiment of the invention.

FIG. 14A illustrates another embodiment of the present invention. This embodiment is similar to the embodiment illustrated in FIG. 14, with the exception that the retainer 316' extends outwardly rather than inwardly. The outward shape of the retainer 316' matches that of the broad exterior periphery of the crimp 322 when the brush 320 is rotated 90°. The broad exterior periphery of the applicator brush crimp 322 on the applicator brush 320 is wider than the lateral width of the applicator well 314. Therefore, the applicator brush 320 is securely held within the applicator well 314 and cannot be easily pulled out of the applicator well 313 after a cover is affixed to the planer surface 323. The enlarged retainer 316 facilitates placement of the applicator brush 320 within the applicator well 314 in the assembly of the package. This embodiment permits placement of the applicator brush 320 within the applicator well 314 at substantially any angular rotation along the longitudinal axis of the applicator brush 320.

Referring to FIG. 15, a cover 326 is applied to the top surface 323. The cover 326 is typically made of a thin flexible sheet material that seals along the entire top surface 323 as hereinbefore described. As illustrated in FIG. 15, the portion of the applicator brush 320 extending beyond the open end or edge of the applicator well 314 is easily held and used to pry up a portion of the cover 326, facilitating easy removal thereof when desired. This easy cover removal feature of the present invention is of great advantage, especially in many medical applications when rubber gloves are used, which would otherwise render it very difficult to separate the cover 326 from the planar surface 323. Upon removal of the cover, the medicament 324 may be easily and conveniently applied whereupon the entire package and applicator can be readily disposed of after use.

Figure 16:
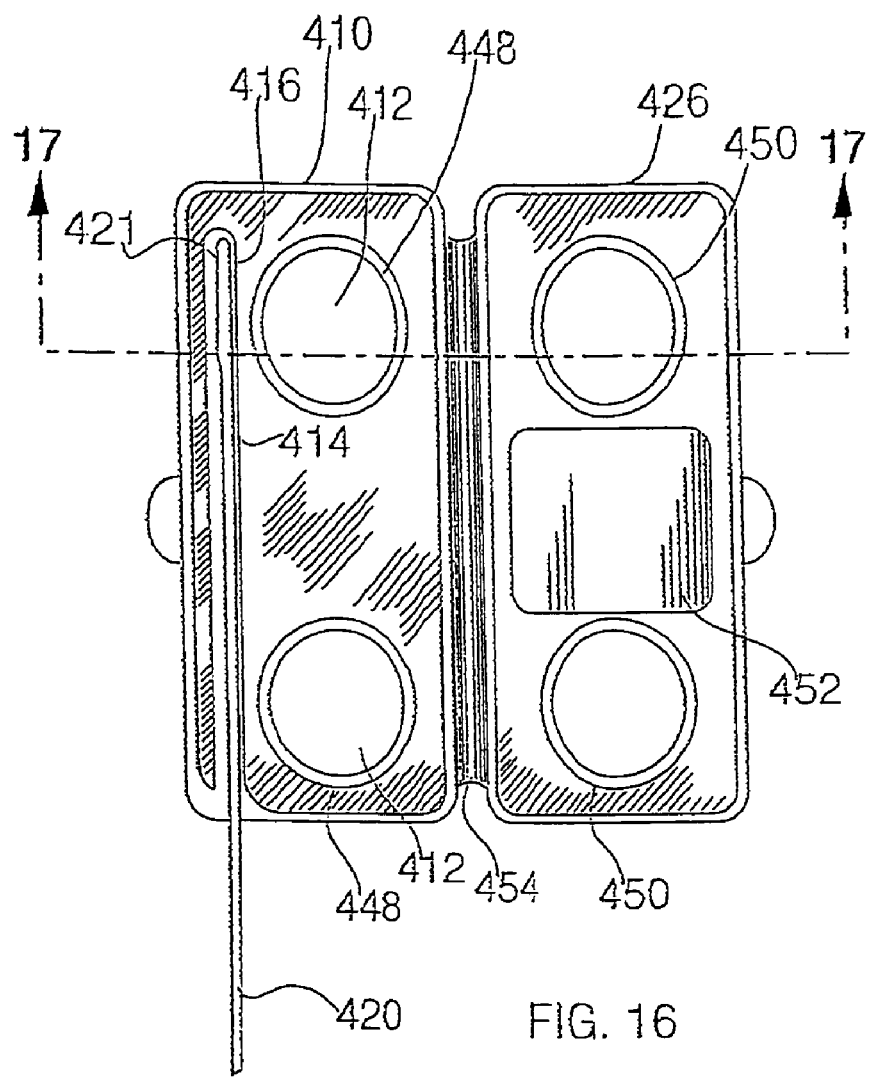
FIG. 16 is a plan view of another embodiment of the invention.
Figure 17:
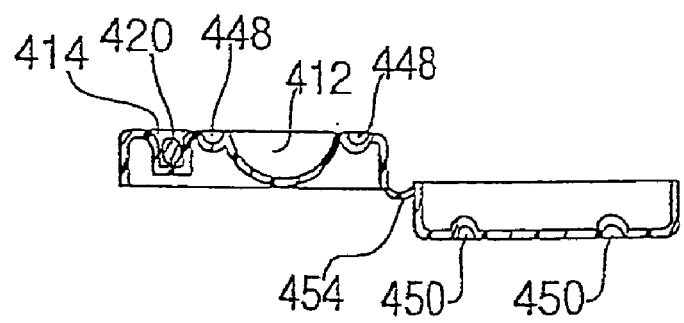
FIG. 17 is a side elevational view of the embodiment illustrated in FIG. 16.

FIGS. 16–17 illustrate another embodiment of the present invention. This embodiment is particularly applicable to procedures requiring the mixing of two or more materials in a particular procedure. Many procedures require the mixing of two materials that chemically interact. In this form, the tray 410 has formed therein at least two medicament wells 412 and an applicator well 414. Within applicator well 414 is a suitable applicating device, e.g. a spatula applicator 420. Spatula applicator 420 has a broad flat portion 421. The broad flat portion 421 has a dimension greater than the diameter of the handle portion of spatula applicator 420. A closed end portion 416 of the applicator well 414 has a depth that is greater than the depth of the portion of the remaining length of the applicator well 414 that receives the handle portion of the spatula. The broader spatula portion 421 of the spatula applicator 420 fits within this deeper closed end portion 416 and forms a means for retaining the spatula applicator 420 within the package or tray 410. Also formed within tray 410 circumscribing the medicament wells 412 are female sealing rings or grooves 448. The tray 410 is provided with a hinged cover 426. The cover 426 is attached with an integral flexible living hinge or web 454. Formed within cover 426 are male or projecting sealing rings 450. Male sealing rings 450 in the closed position of the hinged cover 426 are arranged to mate and interlock with female sealing rings or grooves 448. Also placed on cover 426 is a mixing area 452. The mixing area 452 may optionally be placed on the tray portion 410 between the medicament wells 412.

Figure 18:
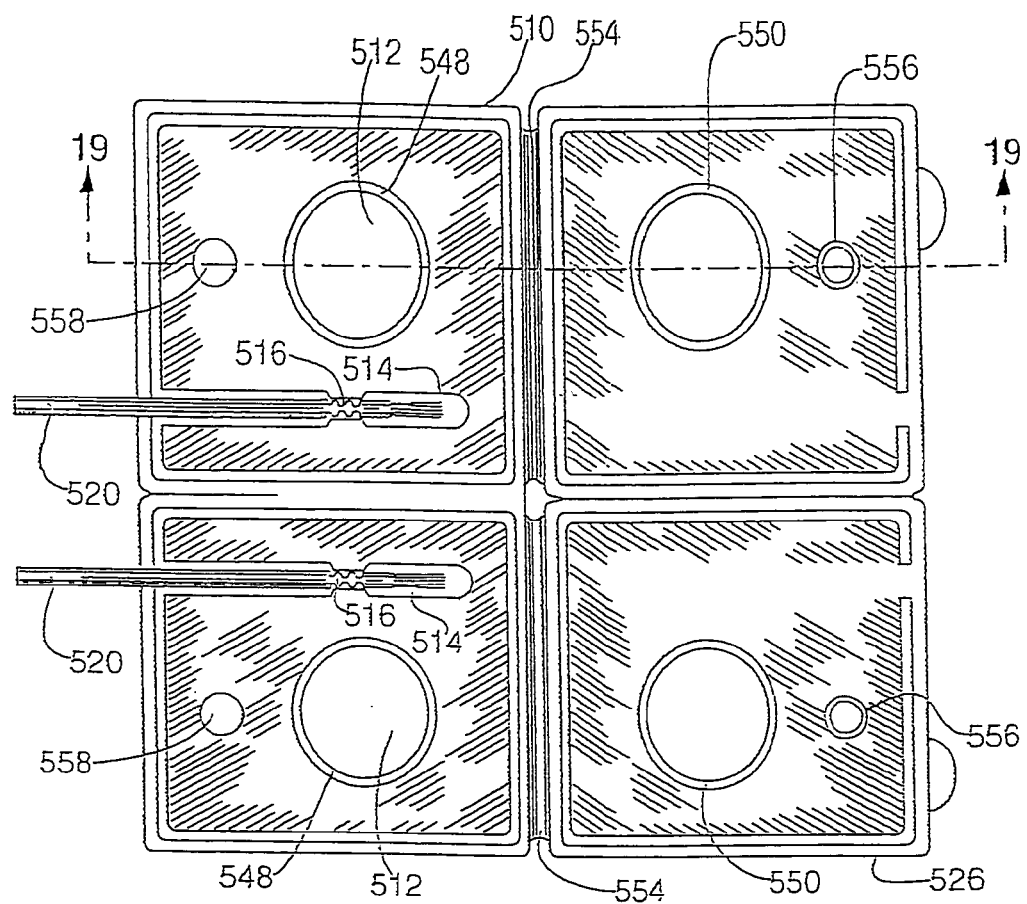
FIG. 18 is a plan view of another embodiment of the invention.
Figure 19:
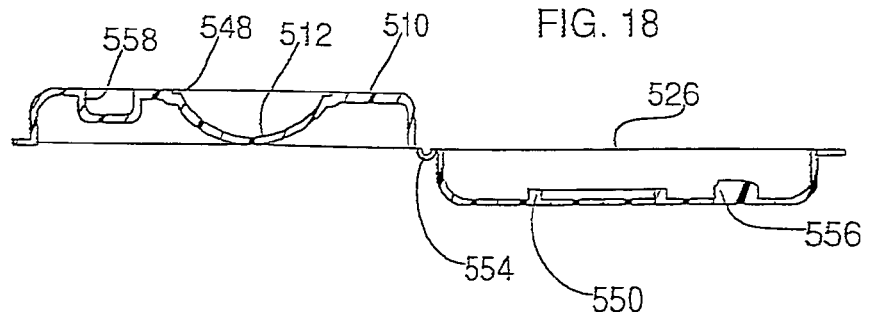
FIG. 19 is a front elevational view of the embodiment illustrated in FIG. 18.
Figure 20:
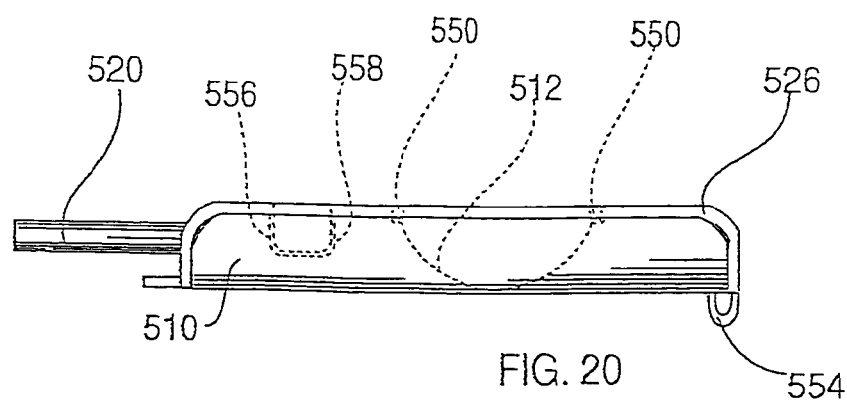
FIG. 20 illustrates the side view of the embodiment of FIG. 18 in the closed or assembled position.

FIGS. 18–20 illustrate another embodiment of the present invention. A tray 510 has formed therein at least two medicament wells 512 and at least two applicator wells 514. Each of the medicament wells 512 have a female sealing ring or groove 548 circumscribing it. Formed within each of the applicator wells 514 is a retainer 516. Retainer 516 protrudes into the applicator well 514 for holding an applicator or brush 520 therein. The retainer, although not illustrated, may also be wider than the width of the applicator well 514 as described for the embodiment shown in FIG. 14A. Adjacent each medicament well 512 is a female locking tab 558. Covers 526 are attached to the tray 510 by integral hinge or web 554. Each of the covers 526 may be opened and closed independently. Formed within each cover 526 is a male sealing ring 550 for sealing its corresponding medicament well in the closed position. The male sealing rings or projection 550 are adapted to mate with corresponding female sealing rings or grooves 548 formed within the tray 510 in the closed position. Associated with each cover 526 is a male locking tab 556. Male locking tabs 556 of the cover 526 are adapted to mate with female locking tabs 558 of the tray in the closed position. This embodiment of the present invention is particularly applicable to a procedure requiring a two-part application of a medicament. In this embodiment, an applicator brush 520 is associated with each of the medicament wells 512. Additionally, some of the medicaments may be light sensitive and need to be applied sequentially. This embodiment provides for covers 526 that can be independently opened and closed as may be needed to permit application of the medicament for one part of the procedure without opening or uncovering the medicament required for a second part of a procedure.

Figure 21:
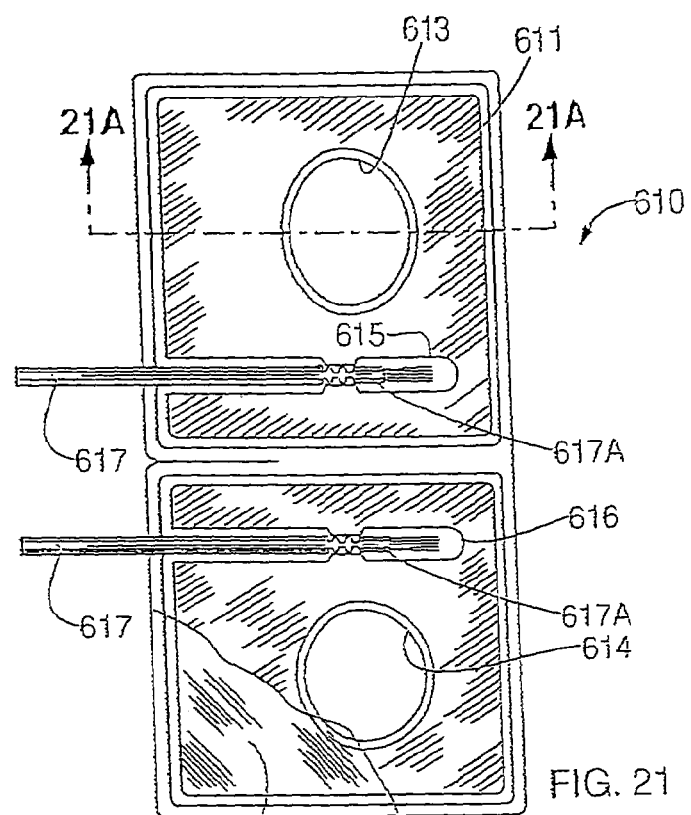
FIG. 21 is a plan view of another embodiment of the invention.
Figure 21A:
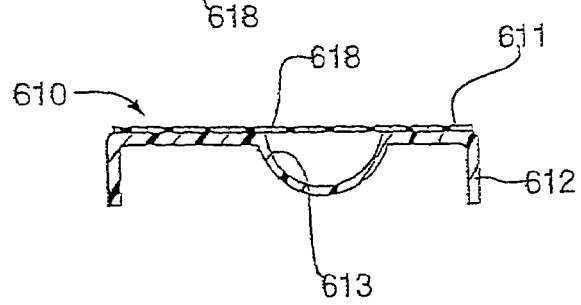
FIG. 21A is a sectional view taken on line 21A—21A on FIG. 21.

FIGS. 21 and 21A illustrate a further embodiment of the invention. In this form, the tray 610 is vacuum formed from a sheet of plastic which is formed with a top or plane surface 611 about which there is formed a circumscribing depending side wall 612. In this form of the invention, the top or plane surface 611 is provided with at least two depressions to define spaced apart wells 613 and 614 which are adapted to receive a suitable medicament or dental material. Frequently in a medical or dental application or procedure, a two-part medicament or material is required. For example, in dentistry, many chemically cured materials are used to perform various dental procedures, which must be kept separated until readied for use. The tray dispenser of FIG. 21 is particularly applicable for unit dispensing such materials. Each such material is placed in each of the wells 613 and 614. The amount of material placed in wells 613 and 614 is sufficient to formulate a unit or single dose. Also formed in the top or plane surface 611 is an elongated recess 615 and 616 arranged to receive a suitable applicator 617, e.g. a brush, spatula and the like, as previously described with respect to FIG. 18. In this form of the invention, a plastic film 618 is adhesively secured to the top plane of the tray to protect and cover the top plane including the wells 613, 614 and the material contained therein and the elongated recess containing the applicating head or end 617A of the respective applicator 617. It will be understood that the covering film 618 may be rendered transparent or light opaque, depending upon the nature and/or characteristics of the material contained in the wells 613, 614. To use the tray dispenser 610 of FIGS. 21, 21A, the user need only to remove the covering film 618 to expose the material in the wells and the associated applicator.

Figure 22:
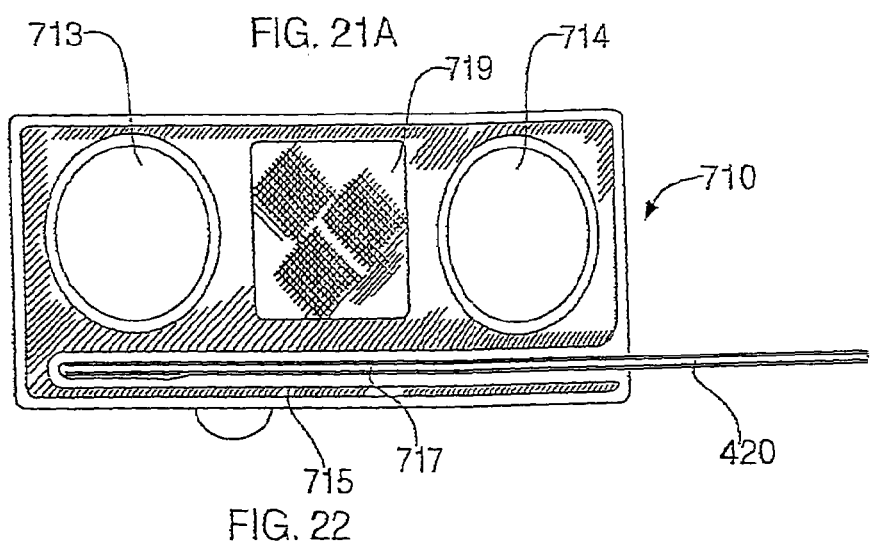
FIG. 22 is a plan view of still another embodiment of the invention.

FIG. 22 is directed to a modified form of the dispenser tray shown in FIG. 21. In this form, the dispenser tray 710 is also in vacuum form similar to that of FIG. 21, except that it may be made somewhat smaller since only one applicator 717 is required. Between wells 713 and 714, there is formed a mixing area 719. The mixing area 719 may be smooth, or if desired the mixing area 719 may be provided with a serrated or roughened surface. The applicator 717 is stowed in an elongated recess 715 extending along the length of the tray 710. With the material placed in the wells and the applicator 717 in place, the tray 710 is covered with a plastic film or sheet and adhesively secured thereto as hereinbefore described.

Figure 23:
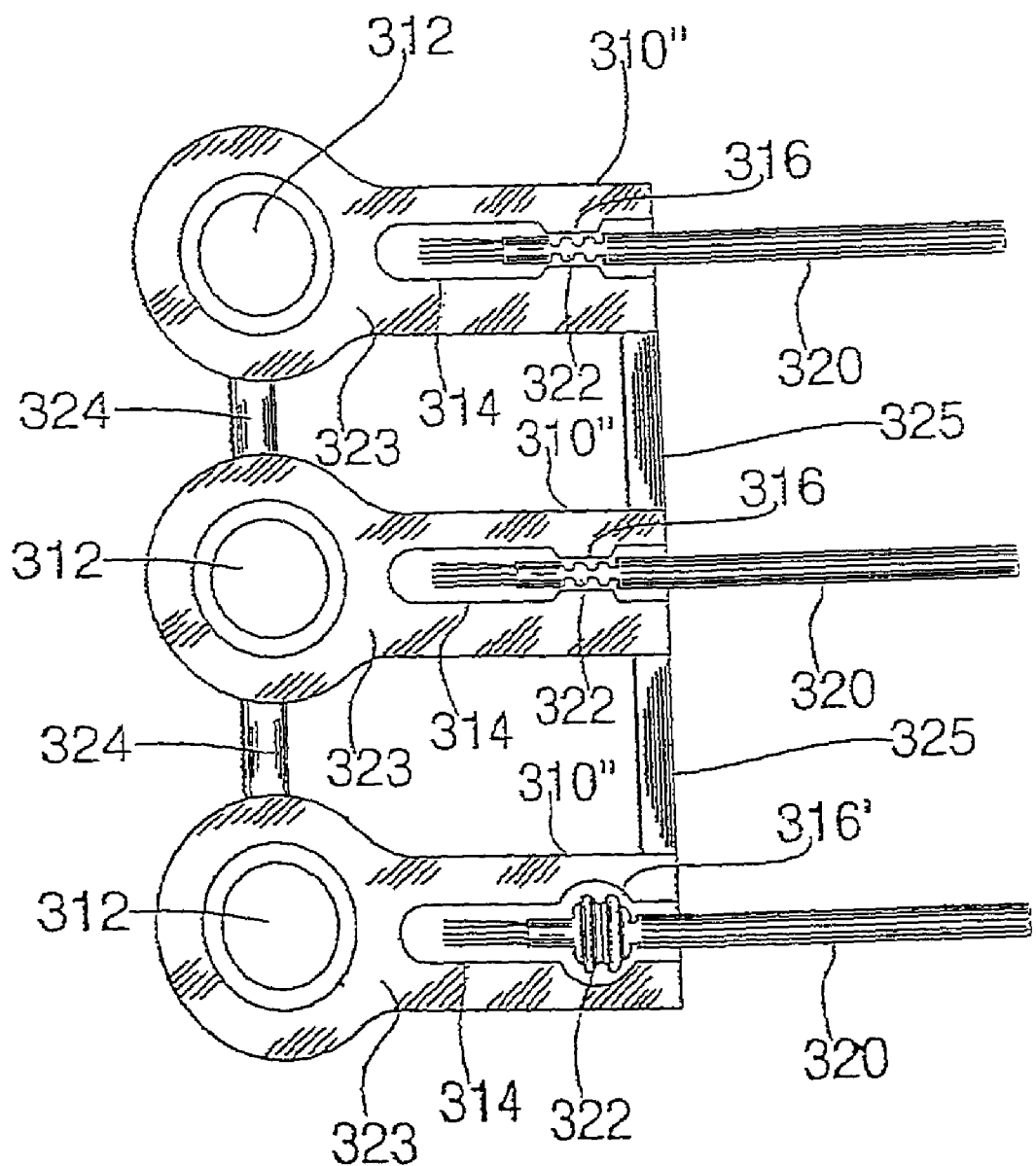
FIG. 23 is a plan view of another embodiment of the invention.

FIG. 23 illustrates a dispenser tray as described with respect to FIG. 14 or 15 wherein the dispenser trays are integrally connected by a front web 324 and a rear web 325. It will be understood that the webs 324 and 325 are provided with a frangible portion to facilitate separating one tray from the other. In this form, the individual trays are chain connected by webs 324 and 325 permitting the trays to be sold in clusters or groups.

Figure 24:
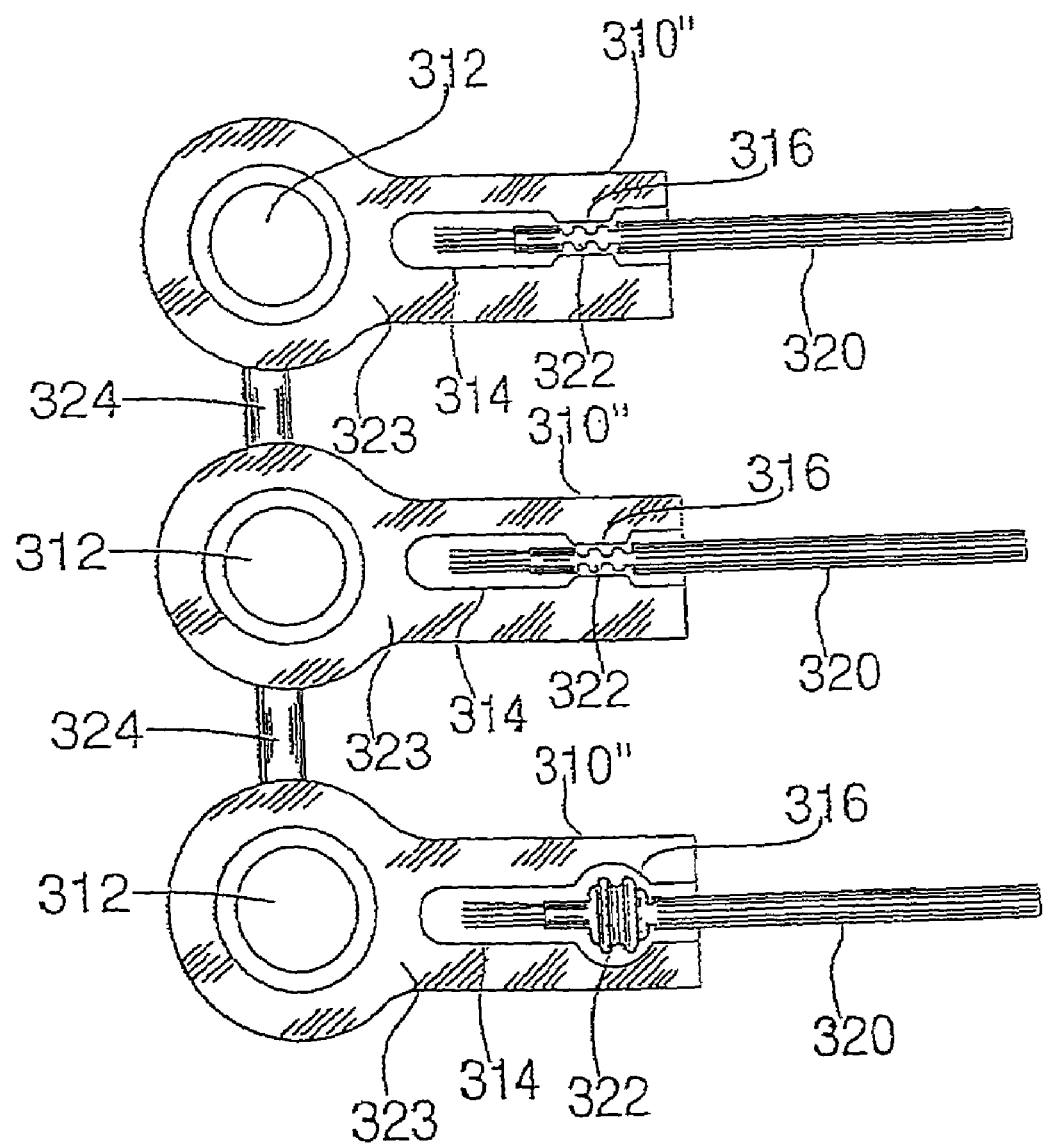
FIG. 24 is a plan view of another embodiment of the invention.

FIG. 24 illustrates the trays as described in FIG. 14 or FIG. 14A integrally connected only by a single web 324.

Figure 25:
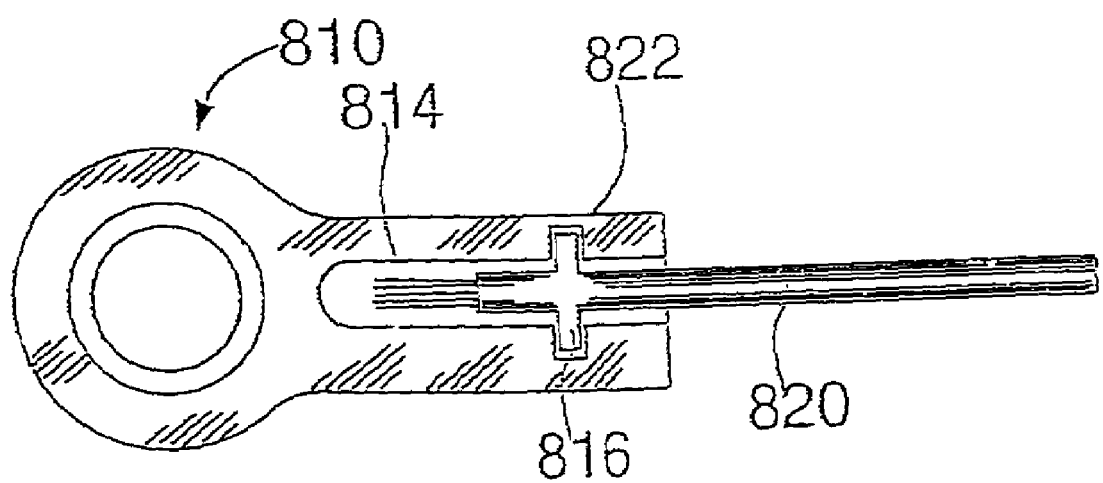
FIG. 25 is a plan view of still another embodiment of the invention.

FIG. 25 illustrates a further embodiment of the invention. This form of the invention is similar to that described with respect to FIG. 14, 14A, or 15 wherein the applicator 820 has been modified to include a flange 822. The recess or applicator well 814 is also modified to provide a recess portion 816 to accommodate the flange 822 of the applicator 820. The arrangement is such that the flange 822 prohibits the applicator 820 from being accidentally or inadvertently pulled out of the dispenser tray 810. In all other respects, the dispenser tray of FIG. 25 is similar to that hereinbefore described.

Figure 26:
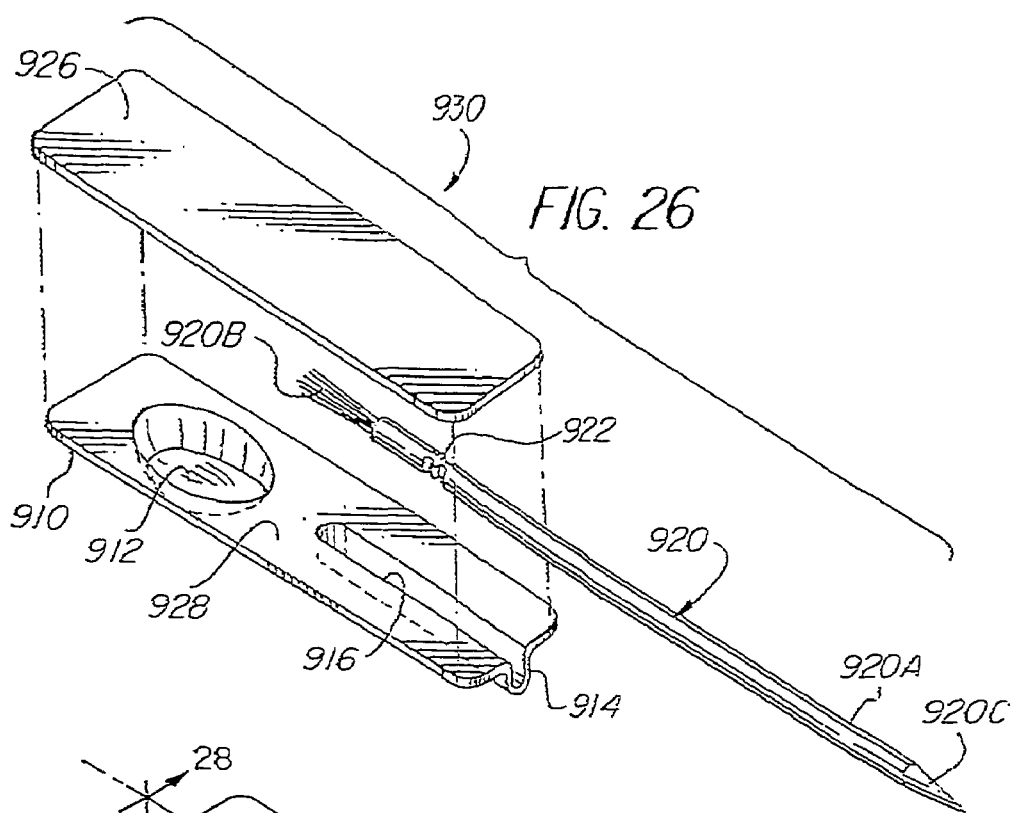
FIG. 26 is an exploded perspective view of a modified embodiment of the invention.
Figure 27:
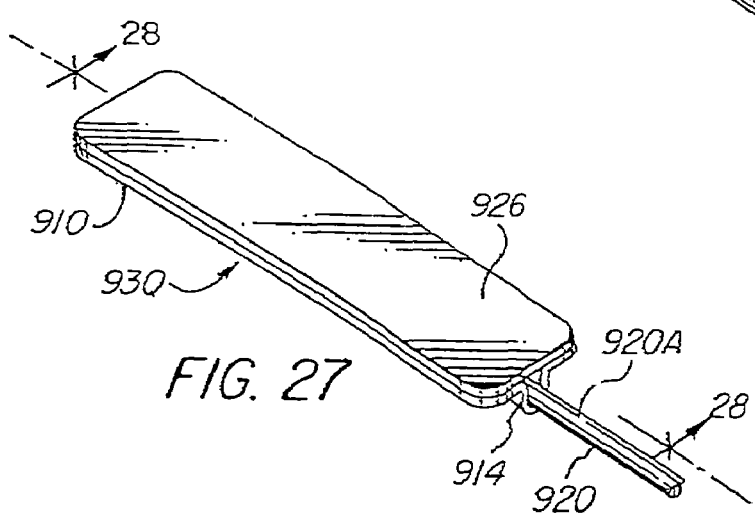
FIG. 27 is an assembled perspective view of the modified embodiment of FIG. 26.
Figure 28:
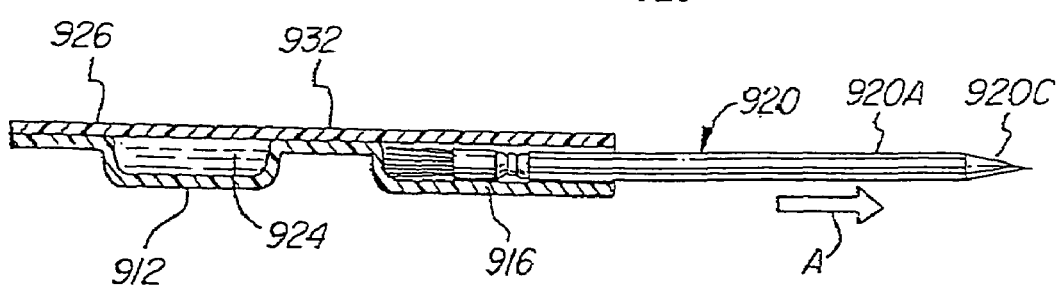
FIG. 28 is a sectional view taken along line 28—28 on FIG. 27.
Figure 29:
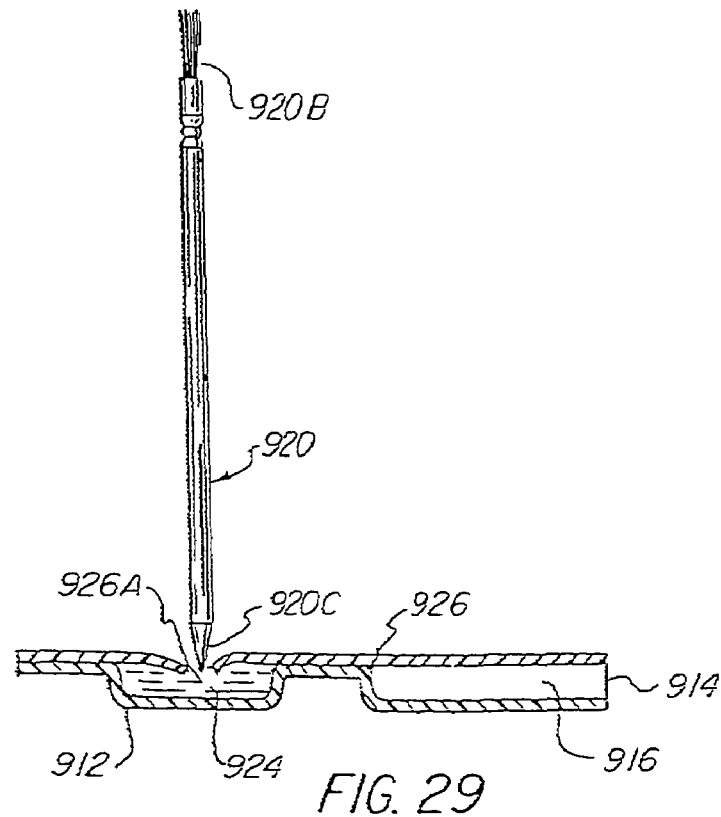
FIG. 29 is a sectional view similar to that of FIG. 28, but illustrating the applicator in the piercing mode.

FIGS. 26 to 29 illustrate a further embodiment of the invention. Referring to FIG. 26, the unit dose dispenser 930 includes a tray 910, which is preferably formed of a suitable plastic which can be readily formed, e.g. by vacuum forming to the shape illustrated. The tray 910 is formed with a material well 912 and an elongated well 916, which is opened at one end as indicated at 914. Circumscribing the respective wells 912 and 916 is a planar surface 928. An applicator 920 is adapted to be received within the applicator well 916. The applicator 920 illustrated has an applicating end portion 920B in the form of a bristle brush. The arrangement is such that when the applicator 920 is positioned in well 916, the elongated handle portion 920A extends through the well opening 914 as seen in FIG. 28. The free end of the handle portion 920A is provided with a pointed or piercing end 920C.

Disposed in the material well 912 is a predetermined amount of a dental material 924 which may be a liquid or fluent type of material. A cover 926 is secured to the planar surface 928 in any manner as hereinbefore described, and which may be adhesively or heat bonded thereto.

In the illustrated embodiment, the applicator 920 is provided with a crimp or flexible hinge 922 adjacent the brush 920B so that in use, the brush or applicating end portion 920B may be bent at an angle relative to the longitudinal axis of the handle 920A.

The arrangement is such that when the material 924 is to be dispensed, the user simply pulls the applicator 920 axially out of the open end 914 of the well 916. With the applicator 920 removed from the well 916, the user can then pierce the cover 926 with the piercing end or point 920C of the applicator 920, as seen or noted in FIG. 29. The piercing of the cover 926 is sufficient to form a hole 926A sufficiently large enough to permit the applicating end 920B to pass therethrough so as to coat the applicating end 920B of the applicator so that the material 924 may be applied to a tooth or the surface to be treated.

This embodiment of the invention is particularly suitable for dispensing a liquid or fluent type of material 924. It is to be noted that the quantity of material 924 is small, and may be as little as a fraction of a gram. Consequently, it has been noted that efforts to remove the cover 926, which is adhesively or heat sealed to the underlying tray 910, may be difficult without causing the liquid 924 in well 912 to be spilled. Therefore, to avoid any possibility of spilling or losing any of the material 924 by any attempt to remove the cover 926 off the tray 910 to expose the well 912 and the material therein, the embodiment of FIGS. 26–29 allows for the cover 926 to be pierced so as to form a hole 926A in the cover to allow access to the liquid material 924 in well 912. In this manner, the user is assured that none of the liquid is spilled or lost in attaining access thereto.

It will also be understood that if the material 924 is light activated, i.e. sets or cures upon exposure to light, the cover may be made light opaque. In such event, the piercing of the cover 926 has the further advantage in that the material 924, if light activated, will have minimal exposure to light while the material is being dispensed, as the hole 926A is relatively small so as to permit only the applicating end of the applicator to pass therethrough. The cover 926 may be formed of a suitable inert plastic film or foil which is imperforate to liquid or fluent type material, yet which can be readily pierced by the piercing end of an applicator.

In the assembled position as seen in FIGS. 27 and 28, the applicator 920, be it a brush, spatula, swab or flocked type applicator, as hereinbefore described, is releaseably retained with the applicator well 916. This is readily attained by maintaining the relative proportions of the handle portion 920A relative to the size of the opening 914 so as to prevent unintentional separation of the applicator from the well 916, yet is rendered readily releaseable from the applicator well 916 by the application of a reasonable pulling force applied to the applicator in an axial direction, as indicated by arrow A in Fig. 28. This can be attained by crimping the end of the tray and/or cover adjacent opening 914 to secure the applicator by sufficient holding force to prohibit unintentional separation, and which holding force may be overcome by the application of a reasonable pulling force applied to the applicator as indicated by arrow A to effect an intentional separation of the applicator from its well 916.

Figure 30:
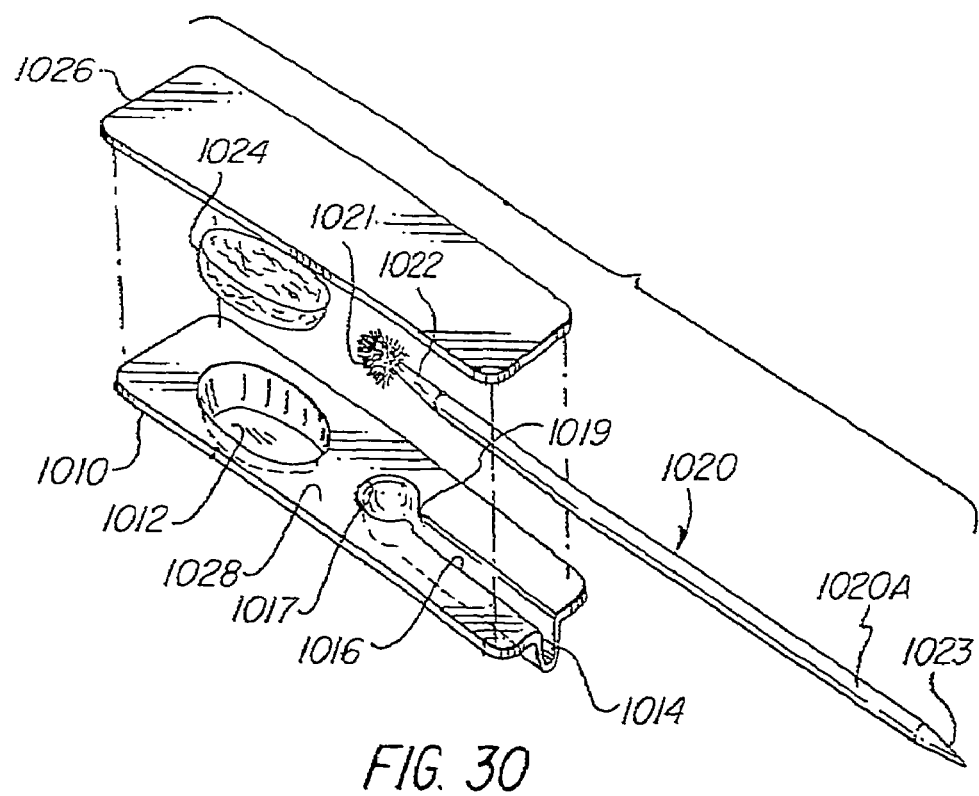
FIG. 30 is an exploded perspective view of another embodiment of the present invention using a flocked applicator.

FIG. 30 is an exploded perspective view of another embodiment of the present invention with a flocked applicator 1020. A tray 1010 has a material well 1012 and an elongated applicator well 1016 formed therein. The elongated applicator well 1016 has an enlarged portion 1017 and a narrowed portion 1019. The enlarged portion 1017 is sized to receive a flocked end 1021 of the flocked applicator 1020. The narrowed portion 1019 is sized to receive a reduced portion 1022 of the flocked applicator. However, it should be appreciated that in most applications the flocked end 1021 may be of sufficiently large size so as to be retained within the applicator well 1016 without the need of narrowed portion 1019. Handle 1020A of he flocked applicator 1020 extend through end opening 1014 in the applicator well 1016. Handle 1020A has a sharp or pointed end 1023. The sharp end 1023 can be used to poke a hole in cover 1026 to access material 1024 located in material well 1012. This is particularly advantageous when the material 1024 is a liquid or low viscosity material. It has been discovered that even though the handle 1020A extending beyond the tray 1010 greatly facilitates the removal of the cover 1026, when a liquid or low viscosity material 1024 is placed in the material well 1012 spillage often occurs when the cover 1026 is removed. Therefore, the sharp or pointed end 1023 can be used to poke or pierce a hole in the cover so that the flock end 1021 can be inserted without removing the cover. This has the additional advantage of helping to prevent the material 1024 from becoming contaminated after opening because of the relatively small opening.

As in FIGS. 11–13, the embodiment illustrated in FIG. 30 could have a passage formed, for example by an adhesive free section, between the material well 1012 and the applicator well 1016. Additionally, should more than one material be desired, additional material wells could be placed in the tray 1012.

Figure 31:
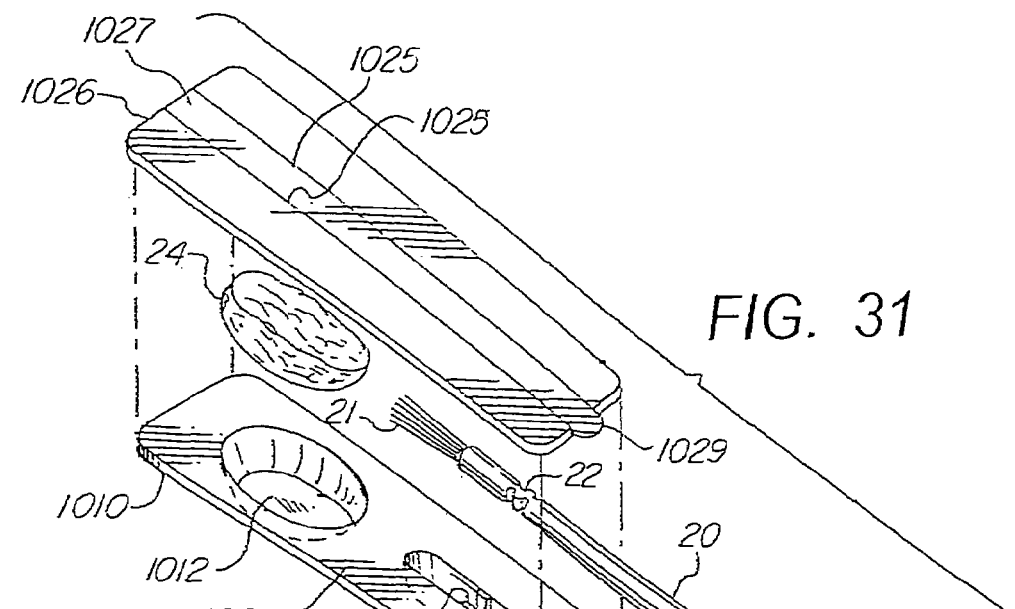
FIG. 31 is a perspective view of another embodiment of the present invention.
Figure 32A:
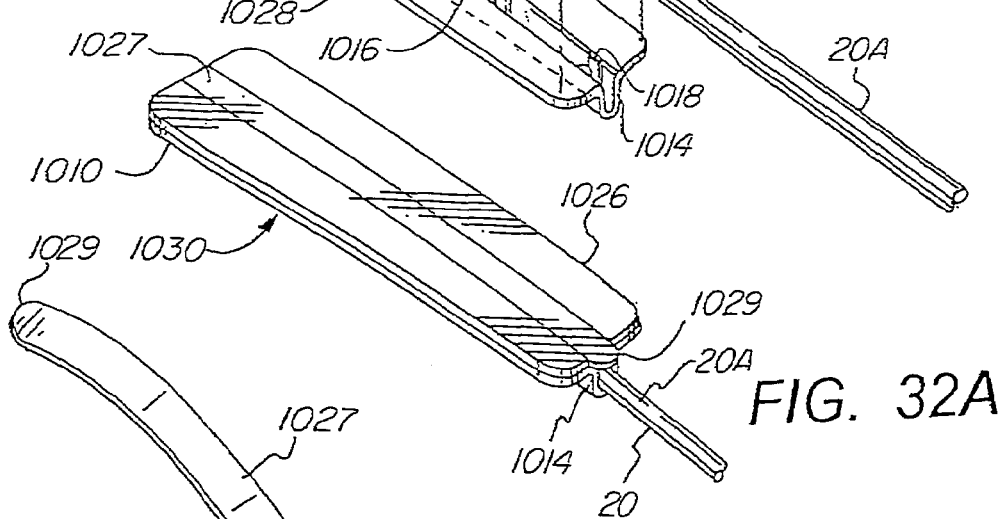
FIG. 32A is a perspective view of assembled embodiment illustrated in FIG. 31.
Figure 32B:
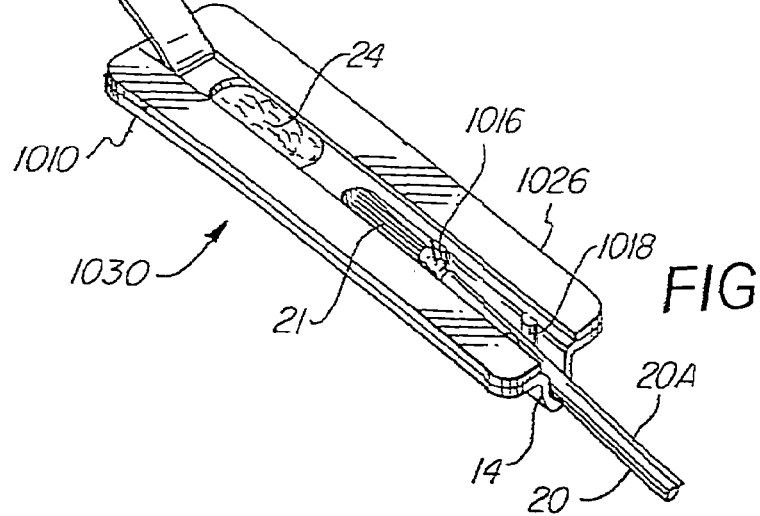
FIG. 32B is a perspective view of the opened dose package illustrated in FIG. 32A.

FIGS. 31–32B illustrate another embodiment of the present invention. In this embodiment, a tray 1010 has a medicament well 1012 and an applicator well 1014 formed in the planar surface 1028 of the tray 1010. The applicator well 1014 preferably has a retainer 1016 and/or a seal 1018 formed therein. A material or a medicament 24 is placed within the well 1012. The applicator 20 may have bristles 21 and a reduced portion or crimp 22 and a handle portion 20A. The reduced portion or crimp 22 may mate with the retainer 1016. The tray 1010 may be made of plastic so that the sides of the applicator well 1014 are somewhat flexible, permitting easy removal of the applicator 20 from the applicator well 1014. Seal 1018 helps prevent the applicator portion or the bristles 21 from being contaminated. The applicator well may be formed with inwardly extending end portions that extend towards one another to define a space slightly less than the diameter of the applicator handle so that the handle fits within the applicator well. This arrangement is such that any unintentional lateral separation of the applicator from the well is resisted until ready for use.

A cover 1026 is placed over the applicator well 1014 and the medicament well 1012. The cover 1026 has a removable strip 1027 along the longitudinal length of the cover 1026. The frangible lines 1025 define the strip 1027. The frangible lines 1025 are weakened portions of the cover 1026 so as to permit the strip 1027 to be separated from the remaining portion of the cover 1026. The strip 1027 may have a tab 1029 on one end to facilitate grasping and separating the strip 1027 from the cover 1026. The frangible lines 1025 may be formed by any conventional process such as scoring or cutting and may even be formed as a different material, which is adhered to a portion of the cover 1026 or any other equivalent means for providing a removable strip or portion of a cover.

FIG. 32A illustrates the assembled dose package 1030 having the cover 1026 formed on the tray 1010 with the applicator handle 20A of the applicator 20 extending from the applicator well 1014. The strip 1027 is initially attached to the cover 1026.

FIG. 32B illustrates the dose package 1030 having the strip 1027 removed from a portion of the cover 1026. The applicator 20 and the material 24 are exposed upon removing the strip 1027. If desired, only the material need be exposed or uncovered. The applicator 20 can easily be removed from the dose package 1030 through the end opening of the applicator well 1014 and used to apply the material 24. The edges of the cover 1030 adjacent the material may be used to wipe the applicator portion or bristles 20 so as to provide an appropriate amount of material on the applicator 20. Accordingly, the width of the strip 1027 may be less than the width of the material well 1012. The applicator portion 21 may be made of any material such as bristles, cotton fiber, flock, or any other material used for applying a material.

Figure 33:
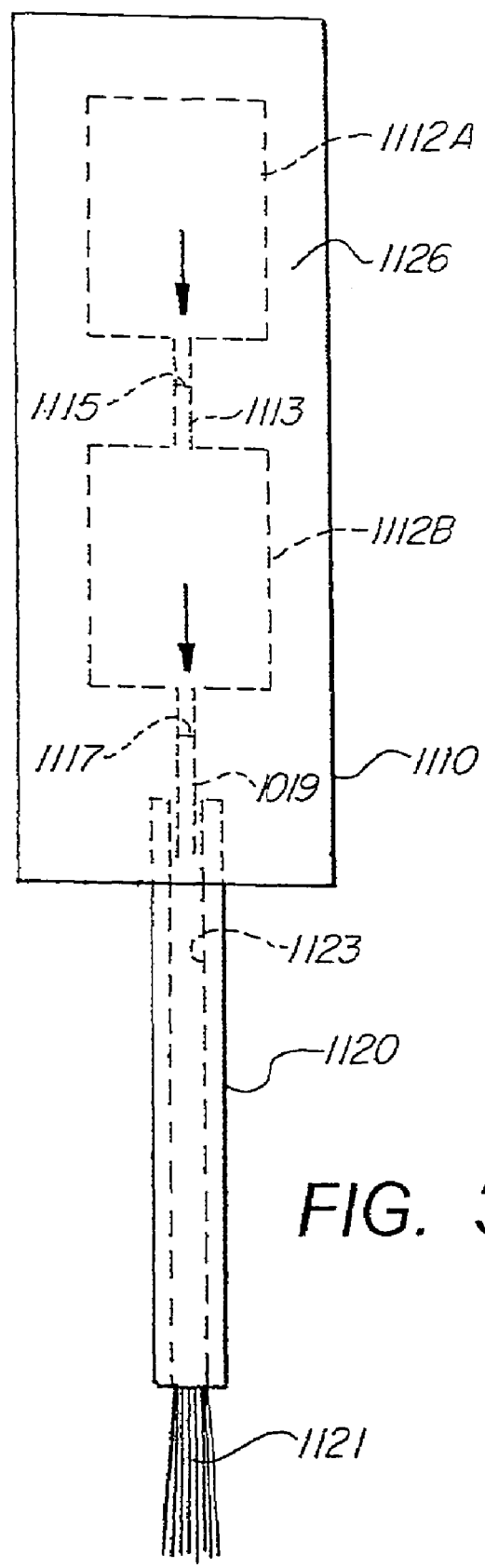
FIG. 33 is a plan view of another embodiment of the present invention.

FIG. 33 illustrates another embodiment of the present invention. In this embodiment, tray 1110 has a plurality of material wells 1112A and 1112B formed therein. The wells 1112A and 1112B are connected to each other through a channel 1113 which may be defined between the cover 1126 and the upper surface of the tray 1110 or by a connecting conduit between the material wells 1112A and 1112B. The channel 1113 interconnecting the material wells 1112A and 1112B preferably has a frangible portion 1115 therein. The frangible portion 1115 prevents the unintentional communication through channel 1113 between the wells 1112A and 1112B. This frangible portion 1115 may be a weakened adhesive area, a releasable adhesive area, a frangible diaphragm or membrane, or other equivalent frangible portion. A cover 1126 is used to cover the wells 1112A and 1112B and to form the channel 1113 defined by the cover 1126 and tray 1110. Formed in one of the wells 1112B is a nozzle 1019. The nozzle 1019 preferably has another frangible portion 1117 formed therein. The frangible portion 1117 may be a breakable seal, diaphragm, removable adhesive or plug, adhesive or restricted portion of the nozzle 1019, or other equivalent frangible portion. The nozzle 1019 is adapted to receive the handle end of an applicator 1120. The handle end of applicator 1120 has a bore 1123 therein. The bore 1123 extends to the applicator end portion or bristles 1121 at the other end of the handle of applicator 1120.

In the embodiment illustrated in FIG. 33, two different materials may be contained in the two different wells 1112A and 1112B. For example, a catalyst and a base may be held in one of each of the wells 1112A and 1112B such that when they are combined, a chemical reaction occurs. Accordingly, the frangible portion or seal between the two wells 1112A and 1112B may be broken and the material contained within well 1112A forced into the well 1112B by squeezing or other equivalent technique. The material may also be mixed in either of the wells through a back and forth or other motion and then, after appropriate mixing, ejected through the nozzle 1019 by breaking the frangible seal 1117. Frangible seal 1117 may be broken by squeezing the well 1112B or by piercing. The nozzle 1019 directs the mixed material through the bore 1123 to the applicator end or bristles 1121 for placement of the material onto a surface. The applicator 1120 may be left connected to the nozzle 1019 or removed there from during application. If remained connected thereto, the material may be continuously applied by folding over the package and gently squeezing the well 1112B. The applicator 1120 may be removed from the tray 1110 by an axial pulling force thereon to overcome any frictional retention or other holding force.

Figure 34:
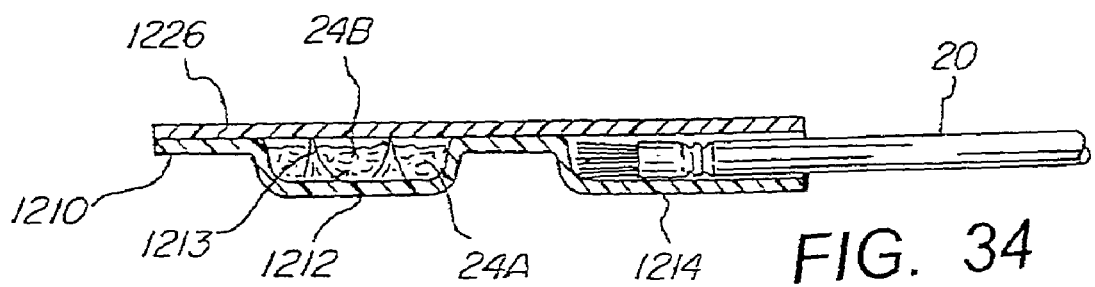
FIG. 34 is a cross section of another embodiment of the present invention.
Figure 35:
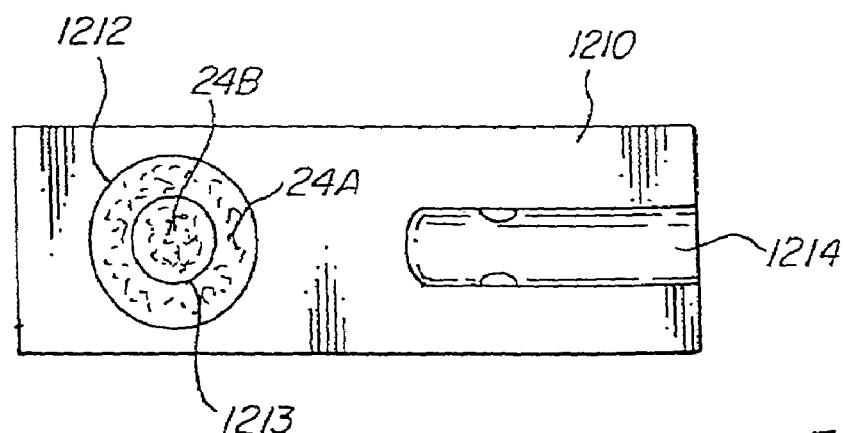
FIG. 35 is a plan view of the embodiment illustrated in FIG. 34.

FIGS. 34 and 35 illustrate another embodiment of the present invention. In this embodiment, a tray 1210 has a material well 1212 and an applicator well 1214 formed therein. A cover 1226 is attached to the top surface of tray 1210, covering the wells 1212 and 1214. Wall 1213 forms another chamber within well 1212. Accordingly, a first material 24A and a second material 24B may be contained within the well 1212; essentially wall 1213 are used to form two separate wells, one surrounding another.

FIG. 35 is a plan view of the embodiment illustrated in FIG. 34 with the cover 1226 and the applicator 20 removed. This embodiment illustrates the concentric wells formed within well 2012. The circular wall 1213 is formed within the circular well 1212 so that materials 24A and 24B are effectively separated. The materials 24A and 24B may be mixed by pushing down on the center of the well 1212 collapsing and the walls 1213. The two different materials 24A and 24B may be a base and a catalyst respectively. The two materials 24A and 24B can then be mixed within the single well 1212.

Figure 36A:
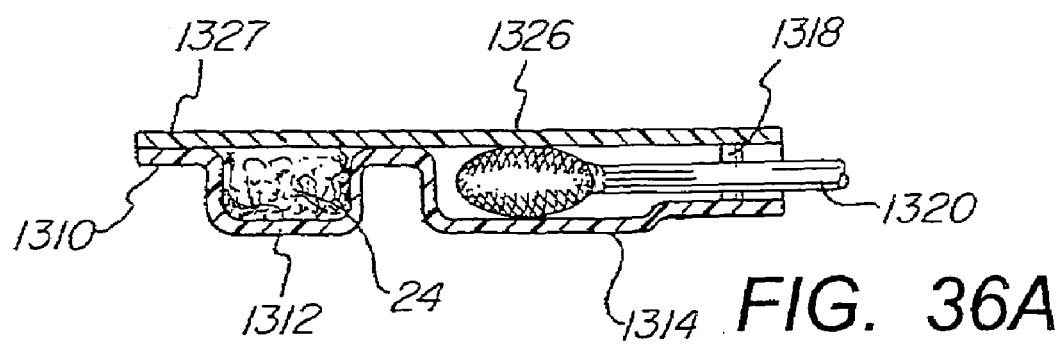
FIG. 36A is a cross section of another embodiment of the present invention.
Figure 36B:
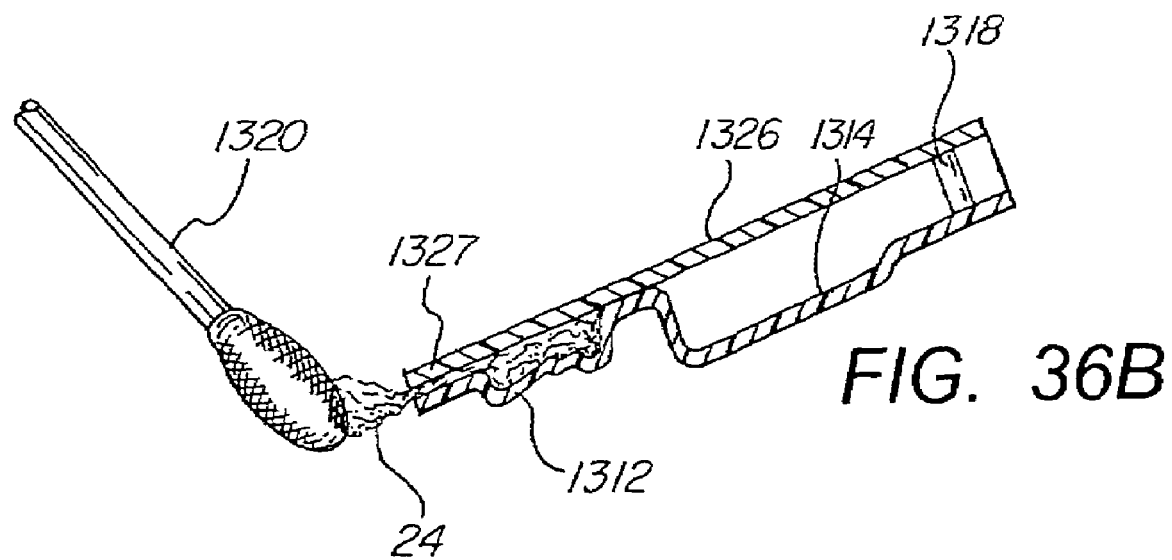
FIG. 36B is a cross section illustrating the use of the embodiment illustrated in FIG. 36A.

FIGS. 36A and 36B illustrate another embodiment of the present invention. In this embodiment, a material may be directly applied to an applicator 1320. A tray 1310 has a material well 1312 and an applicator well 1314 formed therein. The material or medicament well 1312 and the applicator well 1314 are covered by cover 1326. A seal or retainer 1318 may be formed within the side walls of the well 1314 to prevent the applicator 1320 from being contaminated and to aid in holding or frictionally retaining the applicator 1320 within the applicator well 1314. An applicator 1320 is placed within the well 1314. One edge of the material well 1312, having material 24 therein, has a releasable portion 1327. This releasable portion 1327 is a weakened portion formed between the cover 1326 and the tray 1310 so as to permit the material 24 to be pushed there through when the material well 1312 is squeezed.

FIG. 36B illustrates the use of this embodiment. After removal of the applicator 1320 from the applicator well 1314 by pulling it axially past the retainer 1318, the material well 1312 may be squeezed so as to break the releasable portion 1327 and the material 24 dispensed onto the applicator 1320.

Accordingly, it should readily be appreciated that the present invention, in providing a single patient dose or a unit dose package that is easy to use and having a dedicated applicator associated with each medicament clearly facilitates the ease of applying small quantities of material safely and conveniently.

The invention has been particularly described for use as a single dose medicament package with a dedicated applicator so as to be readily disposable after use. However, it will be understood that the invention may also have non-medical or industrial uses. Also, the package described can be used as a sampler for allowing consumers to test or try various types of products. It will also be understood that the medicament can be a liquid, gel or powder or any combination thereof.

While the present invention has been described with respect to various embodiments, various modifications may be made without departing from the spirit and scope of this invention.

What is claimed is:

1. A single dose disposable dispenser for dispensing a material to be applied with an applicator comprising:
    a tray having a material well and an applicator well;
    an applicator placed in the applicator well;
    a wall formed in the material well dividing the material well into a first chamber and a second chamber, the first chamber being surrounded by the second chamber, said wall being deformable permitting selective combining of the first and second chambers; and
    a cover covering the material well and said applicator well,
    whereby different materials are capable of being separated until desired to be mixed together and applied with said applicator.

2. A single dose disposable dispenser as in claim 1 wherein:
    the first and second chambers are concentric.

3. A single dose disposable dispenser as in claim 1 wherein:
    one of the first or second chambers contains a base; and
    another one of the first or second chambers contains a catalyst.

4. A single dose disposable dispenser as in claim 1 further comprising:
    an opening between said tray and said cover through which the handle of said applicator extends outwardly of the applicator well with the handle of said applicator extending beyond an edge of said tray and said cover, and inwardly extending end portions that extend towards one another to define a space less than a diameter of the handle of said applicator, whereby any unintentional lateral separation of said applicator and said tray is resisted.

5. A single dose disposable dispenser as in claim 1 further comprising:
    frangible portions formed in said cover defining a strip extending over the material well.

6. A single dose disposable dispenser as in claim 1 further comprising:
    a releasable portion between the material well and an edge of said tray, whereby the material is capable of being forced there through upon squeezing the material well, whereby the material is capable of being applied directly to an applicator portion of said applicator.

7. A single dose disposable dispenser for dispensing a dental material to be applied in a dental procedure with an applicator comprising:
    a tray having a material well and an applicator well formed therein;
    an applicator placed in the applicator well;
    a wall formed in the material well dividing the material well into a first chamber and a second concentric chamber, the first chamber being surrounded by the second chamber;

a first material placed within the first chamber;

a second material placed within the second concentric chamber, said first material reacting with said second material when combined;

said wall being deformable permitting selective combining of the first and second materials; and a cover covering the material well and said applicator well, whereby first and second materials are capable of being separated until desired to be mixed together, reacted, and applied with said applicator.

8. A single dose disposable dispenser for dispensing a dental material to be applied with an applicator in a dental procedure comprising:

a dental material to be applied in a dental procedure;

an applicator having an applicating end portion and a handle, the applicating end portion being adapted to apply said dental material in the dental procedure;

a tray having a dental material well adapted to receive and containing said dental material to be applied and an applicator well adapted to receive and hold the applicating end portion of said applicator; and a cover attached to said tray covering the dental material well and said dental material and the applicator well and the applicating end portion of said applicator, the applicator well having an opening between said tray and said cover through which the handle of said applicator extends outwardly of the applicator well with the handle of said applicator extending beyond an edge of said tray and said cover, and inwardly extending end portions that extend towards one another to define a space less than a diameter of the handle of said applicator, whereby any unintentional lateral separation of said applicator and said tray is resisted.

* * * * *